United States Patent
Kaga et al.

(10) Patent No.: US 7,074,974 B2
(45) Date of Patent: Jul. 11, 2006

(54) PROCESS FOR THE PRODUCTION OF FLUOROETHANE AND USE OF THE SAME

(75) Inventors: Kazunari Kaga, Kawasaki (JP); Hiromoto Ohno, Kawasaki (JP); Toshio Ohi, Tokyo (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/898,971

(22) Filed: Jul. 27, 2004

(65) Prior Publication Data

US 2005/0065385 A1    Mar. 24, 2005

Related U.S. Application Data

(63) Continuation-in-part of application No. 10/477,322, filed as application No. PCT/JP03/02728 on Mar. 7, 2003.

(60) Provisional application No. 60/364,035, filed on Mar. 15, 2002.

(30) Foreign Application Priority Data

Mar. 11, 2002 (JP) ............................ 2002-064830
Aug. 8, 2003 (JP) ............................ 2003-206761

(51) Int. Cl.
*C07C 17/38* (2006.01)
(52) U.S. Cl. ...................................... 570/177; 570/178
(58) Field of Classification Search ................ 570/177, 570/178
See application file for complete search history.

(56) References Cited

U.S. PATENT DOCUMENTS

| 3,004,908 A | 10/1961 | Haszeldine et al. |
| 5,710,351 A | 1/1998 | Ohno et al. |
| 5,801,294 A | 9/1998 | Sage et al. |

FOREIGN PATENT DOCUMENTS

| CN | 1168875 A | 12/1997 |
| EP | 0 844 226 A1 | 5/1998 |
| EP | 1 110 936 A1 | 6/2001 |
| JP | 3173010 B | 3/2001 |
| WO | WO 03/014047 A1 | 2/2003 |

OTHER PUBLICATIONS

Yoshinaga, Masami et al. "Purification of hydrochlorofluorocarbons and hydrofluorocarbons." Chemical Abstracts, May 10, 1993, vol. 118, No. 19, Columbus, Ohio.

Database WPI, Section Ch, Week 199734, Derwent Publications Ltd., London, GB, AN 1997-367579.

Foreign Office Action (with completed English translation).

*Primary Examiner*—Michael L. Shippen
(74) *Attorney, Agent, or Firm*—Sughrue Mion, PLLC

(57) ABSTRACT

A process comprising fluorinating tetrachloroethylene to obtain a crude pentafluoroethane containing impurities and bringing the crude pentafluoroethane containing impurities into contact with oxygen and/or an oxygen-containing compound in the presence of a catalyst. There can be obtained high-purity pentafluoroethane which can be used as a low-temperature refrigerant or an etching gas or as a starting material for the production of high-purity hexafluoroethane.

27 Claims, No Drawings

PROCESS FOR THE PRODUCTION OF FLUOROETHANE AND USE OF THE SAME

CROSS-REFERENCE TO RELATED APPLICATIONS

This application is continuation in part of application Ser. No. 10/477,322 filed on Nov. 10, 2003, which is the national stage of PCT/JP03/02728 filed on Mar. 7, 2003 and which claims benefit of Provisional Application No. 60/364,035 filed on Mar. 15, 2002.

BACKGROUND OF THE INVENTION

1. Field of the Invention

The present invention relates to a process for the production of pentafluoroethane, a process for producing hexafluoroethane using pentafluoroethane obtained by the production process, and use of the obtained pentafluoroethane.

2. Description of the Related Art

Pentafluoroethane ($CF_3CHF_2$) is used as a low-temperature refrigerant or as an etching gas and is also used as a starting material for the production of hexafluoroethane ($CF_3CF_3$).

As for the production of pentafluoroethane, various methods have been heretofore known. For example, these are:

(1) a method of fluorinating tetrachloroethylene ($CCl_2=CCl_2$) or a fluorinated product thereof with hydrogen fluoride in the presence of a fluorination catalyst (Japanese Unexamined Patent Publication No. 8-268932), (2) a method of subjecting chloropentafluoroethane ($CF_3CClF_2$) to hydrogenolysis (Japanese Patent No. 2,540,409), and (3) a method of reacting a fluorine gas with a halogen-containing ethylene (Japanese Unexamined Patent Publication No. 1-38034).

When these production methods are used, various impurities such as chlorofluorocarbons (CFC), hydrochlorofluorocarbons (HCFC) and hydrofluorocarbons (HFC) are contained in pentafluoroethane which is the objective substance.

In order to obtain high-purity pentafluoroethane, these impurities must be removed as much as possible. Among these impurities, various purification methods have been proposed to remove chlorofluorocarbons not only for the purpose of achieving high purity but also for preventing the depletion of the ozone layer. In particular, chloropentafluoroethane is close to pentafluoroethane in its boiling point and difficult to separate by normal distillation and, therefore, various purification methods have been proposed. For example, these are:

(1) a method by extractive distillation (Japanese International Application Domestic Publication No. 9-508626)

(2) a method of subjecting chloropentafluoroethane contained in pentafluoroethane to hydrogenolysis (Japanese Unexamined Patent Publication No. 8-301801), and (3) a method of removing chloropentafluoroethane contained in pentafluoroethane after fluorinating it with hydrogen fluoride (HF) (Japanese Unexamined Patent Publication No. 6-256234).

Among hydrochlorofluorocarbons and hydrofluorocarbons, difluoromethane ($CH_2F_2$) and 1,1,1-trifluoroethane ($CF_3CH_3$) are known to form an azeotropic mixture or azeotropic like mixture with pentafluoroethane. These compounds are very difficult to separate from pentafluoroethane. When pentafluoroethane is produced by a method containing hydrogenolysis, 1,1,1-trifluoroethane is very often produced as a by-product due to an excess hydrogenation-dehalogenation reaction. This compound is contained in pentafluoroethane in a relatively large amount.

For removing 1,1,1-trifluoroethane contained in pentafluoroethane, a method by extractive distillation is known (Japanese Unexamined Patent Publication No. 9-12487). However, this method by extractive distillation has a problem that a plurality of expensive facilities, such as distillation towers, are necessary and the equipment cost is very high.

SUMMARY OF THE INVENTION

Under these circumstances, an object of the present invention is to provide an industrially advantageous process for producing high-purity pentafluoroethane which can be used as a low-temperature refrigerant or an etching gas or as a starting material for the production of high-purity hexafluoroethane; a process for producing hexafluoroethane using pentafluoroethane produced by the above-described process; and uses of the obtained pentafluoroethane.

As a result of extensive investigations to solve the above-mentioned problems, the present inventors have found that those problems can be solved by a process for producing pentafluoroethane including fluorinating tetrachloroethylene to obtain a crude pentafluoroethane containing impurities, which method includes a step of bringing the crude pentafluoroethane containing impurities into contact with oxygen and/or an oxygen-containing compound in the presence of a catalyst, and thereby completed the present invention.

Therefore, the present invention for example comprises the following:

1. A process for producing pentafluoroethane, comprising the following steps:
   (1) a step of fluorinating tetrachloroethylene to obtain a crude pentafluoroethane, and
   (2) a step of bringing said crude pentafluoroethane into contact with oxygen and/or an oxygen-containing compound in the presence of a catalyst.

2. The process as claimed in item 1, wherein the crude pentafluoroethane used in the step (2) is obtained through a further step of being contacted with hydrogen.

3. The process as claimed in item 1, wherein the temperature in the step (2) is from 150 to 400° C.

4. The process as claimed in item 1, wherein the catalyst is a supported or bulk catalyst mainly comprising trivalent chromium oxide.

5. The process as claimed in item 1, wherein the catalyst is a supported catalyst mainly comprising at least one metal selected from the group consisting of palladium, rhodium, ruthenium, rhenium, platinum and gold.

6. The process as claimed in item 4 or 5, wherein the support for use in the supported catalyst is alumina, fluorinated alumina or zeolite.

7. The process as claimed in item 1 or 2, wherein said crude pentafluoroethane comprises at least one compound selected from the group consisting of fluoromethane, difluoromethane, fluoroethane, 1,1-difluoroethane, 1,2-difluoroethane, 1,1,1-trifluoroethane and 1,1,2-trifluoroethane as impurities.

8. The process as claimed in item 1, wherein the total amount of impurities contained in said crude pentafluoroethane is 2 vol % or less.

9. A process for producing pentafluoroethane, comprising bringing a crude pentafluoroethane into contact with oxygen and/or an oxygen-containing compound at 150 to 400° C. in the presence of a catalyst mainly comprising trivalent chromium oxide, and then separating impurities by distillation.

10. A process for producing pentafluoroethane, comprising bringing a crude pentafluoroethane into contact with oxygen and/or an oxygen-containing compound at 150 to 400° C. in the presence of a supported catalyst mainly comprising at least one metal selected from the group consisting of palladium, rhodium, ruthenium, rhenium, platinum and gold, and then separating impurities by distillation.

11. The process as claimed in item 9 or 10, wherein said crude pentafluoroethane comprises at least trifluoroethane as impurities.

12. The process as claimed in item 9 or 10, wherein the concentration of oxygen and/or oxygen-containing compound is from 0.1 to 20 vol %.

13. A pentafluoroethane having a total impurity amount of 500 vol ppm or less, which is obtained by the process claimed in items 1, 9, or 10.

14. The pentafluoroethane as claimed in item 13, wherein the content of trifluoroethane contained as an impurity is 100 vol ppm or less.

15. A refrigerant comprising the pentafluoroethane claimed in item 13 or 14.

16. A process for producing hexafluoroethane, comprising the following steps:
  (1) a step of fluorinating tetrachloroethylene to obtain a crude pentafluoroethane,
  (2) a step of bringing said crude pentafluoroethane into contact with oxygen and/or an oxygen-containing compound in the presence of a catalyst to obtain pentafluoroethane, and
  (3) a step of reacting the pentafluoroethane obtained through the step (2) with a fluorine gas to obtain hexafluoroethane.

17. The process as claimed in item 16, wherein said crude pentafluoroethane used in the step (2) is obtained through a further step of being contacted with hydrogen.

18. A process for producing pentafluoroethane including a step of bringing crude pentafluoroethane into contact with oxygen or an oxygen-containing compound in the presence of a catalyst and with a moisture content included in the reaction substrate gas in said step of not more than 2 vol %.

19. The process as claimed in item 18, wherein said crude pentafluoroethane is one obtained by a fluorination reaction for fluorinating tetrachloroethylene or its fluorinated product in the presence of a fluorination catalyst using hydrogen fluoride.

20. The process as claimed in item 19, wherein the crude pentafluoroethane is obtained through said fluorination reaction, then a reaction of contact with hydrogen.

21. The process as claimed in item 20, wherein said crude pentafluoroethane comprises at least one compound selected from the group consisting of fluoromethane, difluoromethane, fluoroethane, 1,1-difluoroethane, 1,2-difluoroethane, 1,1,1-trifluoroethane and 1,1,2-trifluoroethane as impurities.

22. The process as claimed in item 18, wherein the total amount of impurities contained in said crude pentafluoroethane is 2 vol % or less.

23. The process as claimed in item 18, wherein the temperature in said step is from 150 to 400° C.

24. The process as claimed in item 18, wherein the concentration of oxygen and/or oxygen-containing compound in the reaction substrate gas is from 0.1 to 20 vol %.

25. The process as claimed in item 18, wherein the catalyst used in said step is a supported or bulk catalyst mainly comprising trivalent chromium oxide.

26. The process as claimed in item 18, wherein the catalyst used in said step is a supported catalyst mainly comprising at least one metal selected from the group consisting of palladium, rhodium, ruthenium, rhenium, platinum and gold.

27. The process as claimed in item 25 or 26, wherein the support for use in the supported catalyst is alumina, fluorinated alumina or zeolite.

28. The process as claimed in item 18, wherein said step is performed, then purification is performed by distillation.

29. A pentafluoroethane having a total impurity amount of 400 vol ppm or less, which is obtained by the process claimed in item 18.

30. The pentafluoroethane as claimed in item 29, wherein the content of trifluoroethane contained as an impurity is 100 vol ppm or less.

31. A refrigerant comprising the pentafluoroethane claimed in item 29.

32. A process for producing hexafluoroethane, comprising the following steps:
  (1) a step of bringing crude pentafluoroethane obtained by a fluorination reaction of fluorinating tetrachloroethylene or its fluorinated product in the presence of a fluorination catalyst into contact with an oxygen and/or oxygen-containing compound in the presence of a catalyst in a system with moisture of not more than 2 vol % and
  (2) a step of reacting the pentafluoroethane obtained through the step (1) with a fluorine gas.

33. The process as claimed in item 32, wherein said crude pentafluoroethane used in the step (1) is obtained through said fluorination reaction, then a reaction of contact with hydrogen.

DETAILED DESCRIPTION OF THE INVENTION

The present invention is described in detail below.

Pentafluoroethane can be produced by a method of fluorinating tetrachloroethylene or a fluorinated product thereof with hydrogen fluoride (HF) or a method of subjecting chloropentafluoroethane to hydrogenolysis. Whichever method is used for the production, the pentafluoroethane obtained through a general purification step such as distillation contains as an impurity chloropentafluoroethane which is difficult to separate from pentafluoroethane since it forms an azeotropic mixture or azeotropic like mixture with pentafluoroethane. Separation of this is required from the standpoint of obtaining high purity and the standpoint of preventing depletion of the ozone layer.

With respect to the method for separating chloropentafluoroethane contained in pentafluoroethane, for example, a method using extractive distillation, a method using hydrogenolysis, a method using adsorption, etc. have been proposed as described above. Among these methods, the method using hydrogenolysis is preferably used as a method of producing pentafluoroethane more inexpensively including the equipment cost. As a problem when selecting a method including a hydrogenolysis step as a method of producing pentafluoroethane, new production of hydrofluorocarbons (HFC) difficult to separate from pentafluoroethane due to an excess hydrogenation reaction may be mentioned. In particular, it is known that difluoromethane and 1,1,1-trifluoroethane are very close to pentafluoroethane in boiling points and form azeotropic mixtures or azeotropic like mixtures and are substancies difficult to separate from pentafluoroethane when using a general purification method such as distillation. As a method for separating and refining HFCs contained in pentafluoroethane, as explained above, the method by extractive distillation has been proposed, but this method has a problem that a plurality of expensive facilities, such as distillation towers, are necessary and the equipment cost is very high.

The production process of pentafluoroethane of the present invention comprises (1) a step of fluorinating tetrachloroethylene to obtain a crude pentafluoroethane containing impurities and (2) a step of bringing the crude pentafluoroethane into contact with oxygen and/or an oxygen-containing compound in the presence of a catalyst. The method for the step (1) is not particularly limited and, for example, tetrachloroethylene may be fluorinated through two steps using hydrogen fluoride (HF) in the presence of a catalyst to obtain a crude pentafluoroethane.

As the oxygen or oxygen-containing compound for contact with the crude pentafluoroethane, oxygen gas, air, $O_3$, $N_2O$, NO, $NO_2$, etc. can be used. Use of oxygen gas or air is preferable.

The crude pentafluoroethane is preferably one obtained by a fluorination reaction for fluorination of tetrachloroethylene or its fluorinated product using hydrogen fluoride in the presence of a fluorination catalyst. Further, said crude pentafluoroethane is more preferably one obtained by said fluorination reaction, then a reaction bringing the product into contact with hydrogen.

As the crude pentafluoroethane, when using pentafluoroethane obtained using a method including a hydrogenolysis comprising contact with hydrogen, if using the process of production of the present invention while still including the excessive hydrogen at the time of the hydrogenolysis, there is the possibility of formation of an explosive mixed gas with oxygen and/or an oxygen-containing compound, so it is preferable that the excessive hydrogen be removed before use for the reaction. Further, if hydrogen chloride and/or hydrogen fluoride is copresent when using the process of production of the present invention, it was observed that the conversion rate of the hydrofluorocarbons falls. Therefore, it is preferable to remove the hydrogen chloride and/or hydrogen fluoride contained in the crude pentafluoroethane from the crude pentafluoroethane, then bring the result into contact with the oxygen and/or oxygen-containing compound. As the method for removing these acid contents, it is possible to use a known method. For example, the method using distillation, the method using an alkali scrubber, the method of contact with a deacidification agent, etc. may be mentioned, but the method using an alkali scrubber is general and preferred.

If performing the step of bring crude pentafluoroethane into contact with oxygen and/or an oxygen-containing compound in the presence of a catalyst according to the present invention, for example difluoroethane or 1,1,1-trifluoroethane contained in pentafluoroethane under the reaction represented by the following formula (a) or (b) to be oxidized and is converted to $CO_2$ etc. The main oxidation product is $CO_2$ and as a by-product, HF is produced.

$$CH_2F_2 + O_2 \rightarrow CO_2 + 2HF \quad \text{formula (a)}$$

$$CF_3CH_3 + 2O_2 \rightarrow 2CO_2 + 3HF \quad \text{formula (b)}$$

The compound which is converted to $CO_2$ by this reaction includes fluoromethane, difluoromethane, fluoroethane, 1,1-difluoroethane, 1,2-difluoroethane, 1,1,1-trifluoroethane, 1,1,2-trifluoroethane and the like. The pentafluoroethane produced using a method based on hydrogenolysis at the step of production or purification usually contains these compounds in a total amount of approximately thousands of vol ppm. These impurities must be removed to obtain high purity.

The total amount of hydrofluorocarbon impurities contained in the pentafluoroethane used in the present invention is preferably 2 vol % or less, more preferably 0.5 vol % or less, still more preferably 0.3 vol % or less. If the concentration of hydrofluorocarbons exceeds 2 vol %, the reaction temperature must be made higher and the lifetime of the catalyst may become shorter.

The catalyst used for the reaction is preferably (i) a supported or bulk catalyst mainly comprising trivalent chromium oxide or (ii) a supported catalyst mainly comprising at least one metal selected from the group consisting of palladium, rhodium, ruthenium, rhenium, platinum and gold. Examples of the raw material which can be used include these metals and oxides and salts of these metals. Examples of the support which can be used for the supported catalyst include alumina, fluorinated alumina and zeolite.

As the method for preparing the bulk catalyst (i) mainly comprising trivalent chromium oxide, for example, the method of adding dropwise a basic substance such as ammonia in an aqueous solution of chromium metal salt to precipitate chromium hydroxide, washing/filtering/drying the precipitate, molding the obtained chromium hydroxide, and heat-treating the molded article in the presence of an inert gas such as nitrogen may be mentioned. As the method for preparing the supported catalyst (ii) mainly comprising palladium, rhodium, ruthenium, rhenium, platinum and/or gold, for example, the method of dissolving a salt of the metal in a water-soluble solvent such as water, methanol and acetone, immersing a support in the solution to adsorb necessary elements, distilling off the solvent and reducing the support with hydrogen under heat may be mentioned.

The temperature in the step of bringing the crude pentafluoroethane into contact with oxygen and/or an oxygen-containing compound in the presence of a catalyst is preferably a range from 150 to 400° C., more preferably a range from 180 to 370° C. If the reaction temperature exceeds 400° C., the catalyst may have a short lifetime and the number of kinds, and amount, of by-products not ascribable to the main reaction may increase. Further, a decomposition reaction of the pentafluoroethane mainly comprising the reaction substrate gas occurs and the amount of loss of pentafluoroethane increases, so this is not preferable from an economical standpoint.

The concentration of oxygen and/or oxygen-containing compound contained in the reaction substrate gas is preferably from 0.1 to 20 vol %. If the concentration of the above compound is less than 0.1 vol %, the conversion rate disadvantageously decreases due to insufficiency of oxygen necessary for the reaction, though this varies depending on the kind and amount of hydrofluorocarbons contained as an impurity in pentafluoroethane. On the other hand, if the oxygen concentration exceeds 20 vol %, an excess reaction proceeds to cause a decomposition reaction of the pentafluoroethane mainly comprising the reaction substrate gas occurs and the amount of loss of pentafluoroethane increases, so this is not preferable from an economical standpoint.

The production process of pentafluoroethane of the present invention can be performed under the above-described reaction conditions, however, the reaction product contains $CO_2$, by-products not ascribable to the main reaction, such as hydrofluorocarbons, and acid contents such as HF, other than pentafluoroethane, and $CO_2$ and acid contents are preferably removed.

The acid contents may be removed, for example, by a method of bringing the reaction product into contact with a purifying agent or a method of bringing the reaction product into contact with water, an alkali aqueous solution or the like. The gas from which the acid contents are removed is preferably dehydrated using a dehydrating agent such as zeolite and then distilled to remove $CO_2$ and simultaneously those by-products not ascribable to the main reaction.

Further, the present invention provides a process for producing pentafluoroethane, comprising bringing a crude pentafluoroethane into contact with oxygen and/or an oxygen-containing compound at 150 to 400° C. in the presence of a catalyst mainly comprising trivalent chromium oxide, and then separating impurities by distillation.

Further, the present invention provides a process for producing pentafluoroethane, comprising bringing a crude pentafluoroethane into contact with oxygen and/or an oxygen-containing compound at 150 to 400° C. in the presence of a supported catalyst mainly comprising at least one metal selected from the group consisting of palladium, rhodium, ruthenium, rhenium, platinum and gold, and then separating impurities by distillation.

The method for purification after the reaction is not particularly limited and the purification can be performed by commonly used distillation. With respect to the distillation method, for example, the following method may be used.

After the crude pentafluoroethane is contacted with oxygen and/or an oxygen-containing compound at 150 to 400° C. in a reactor, the resulting gas is introduced into a distillation tower. The inner pressure of the distillation tower is preferably from atmospheric pressure to 2 MPa. If the inner pressure is less than atmospheric pressure, a facility of reduced pressure system is disadvantageously necessary, whereas if it exceeds 2 MPa, a facility of high pressure system is necessary and this is not preferred. For example, in the case where the above-described catalytic reaction is performed using oxygen, a low boiling fraction containing oxygen is extracted from the top of the distillation tower and a high boiling fraction is extracted from the bottom of the distillation tower. At this time, the components extracted from the top and bottom sometimes contain pentafluoroethane which is the objective component. If this is so, respective components may be introduced into separate distillation towers and purified to recover the pentafluoroethane. When the component separated here is an intermediate for the production of pentafluoroethane, the component may be returned to the reaction step and re-used.

By such purification, pentafluoroethane having a higher purity can be obtained. The content of impurities contained is 500 vol ppm or less. The pentafluoroethane having a purity of 99.95 vol % or more can be analyzed by gas chromatography (GC) using TCD method or FID method, or gas chromatography-mass spectrometry (GC-MS).

Further, the present invention provides a process for producing pentafluoroethane including the step of bringing crude pentafluoroethane into contact with oxygen and/or an oxygen-containing compound in the presence of a catalyst, where the moisture contained in the reactive substrate in the step is not more than 2 vol %.

When the moisture contained in the reactive substrate is over 2 vol %, the conversion rate of hydrofluorocarbons falls. The moisture contained in the reactive substrate is preferably not more than 1.5 vol %.

As explained above, when using pentafluoroethane obtained using a method including hydrogenolysis bringing a substance in contact with hydrogen as the crude pentafluoroethane, if using an alkali scrubber for removing the acid ingredient, some moisture remains in the outlet gas depending on the temperature of the circulating alkali solution. This process is a process for removing the hydrofluorocarbons contained as impurities by keeping the moisture contained in the reactive substrate at not more than 2 vol % when performing the step of bringing crude pentafluoroethane and oxygen and/or an oxygen-containing compound into contact in the presence of the catalyst so as to remove the hydrofluorocarbons contained as impurities, so the moisture in the reactive substrate is made not more than 2 vol % using the method of using a deoxygenation agent such as a molecular sieve or silica gel, the method of lowering the temperature of the pentafluoroethane to less than 18° C. so as to condense and separate the moisture.

By the above process, it is possible to obtain a high purity pentafluoroethane. The content of the impurities contained in the obtained pentafluoroethane is not more than 400 vol ppm. Next, an explanation will be given of the use of the pentafluoroethane obtained using the process of the present invention explained above.

The high-purity pentafluoroethane can be used as a substitute for chlorodifluoromethane ($CHClF_2$) which is a currently-used working fluid for low-temperature refrigerators, and also can be used as a raw material of mixed refrigerants which are other substitutes for chlorodifluoromethane, such as difluoromethane/pentafluoroethane/1,1,1,2-tetrafluoroethane and difluoromethane/pentafluoroethane.

Furthermore, the high-purity pentafluoroethane can be used as a starting material for the production of high-purity hexafluoroethane. Particularly, in the process of producing hexafluoroethane by a reaction of pentafluoroethane with a fluorine gas ($F_2$), when high-purity pentafluoroethane is used as a starting material, production of impurities which are difficult to separate from hexafluoroethane can be prevented, the latitude in setting the fluorination reaction conditions can be enlarged, the reaction can be stably controlled and the purification step can be simplified.

Accordingly, the present invention provides a process for producing hexafluoroethane, comprising (1) a step of fluorinating tetrachloroethylene to obtain a crude pentafluoroethane, (2) a step of bringing the crude pentafluoroethane into contact with oxygen and/or an oxygen-containing compound in the presence of a catalyst, and (3) a step of reacting the pentafluoroethane obtained through the step (2) with a fluorine gas.

The crude pentafluoroethane used in the step (2) is preferably obtained through a further step of being contacted with hydrogen.

Therefore, the present invention further provides a process for producing hexafluoroethane characterized by including (1) the step of bringing crude pentafluoroethane, obtained by a fluorination reaction for fluorinating tetrachloroethylene or its fluorinated product using hydrogen fluoride in the presence of a fluorination catalyst, into contact with oxygen and/or an oxygen-containing compound in the presence of a catalyst with a moisture content of not more than 2 vol % and (2) the step of reacting the pentafluoroethane obtained through step (1) with fluorine gas.

The crude pentafluoroethane used at step (1) is preferably one obtained through the step of contact with hydrogen.

The high-purity pentafluoroethane or a mixed gas thereof, with an inert gas such as He, $N_2$ and Ar, HCl, $O_2$, $H_2$ or the like, can be used as an etching gas in an etching step in the process of producing a semiconductor device. In the process of producing a semiconductor device such as an LSI, a TFT and an organic EL device, a thin or thick film is formed using a CVD method, a sputtering method or a vapor deposition method and a circuit pattern is formed by etching, where a mixed gas containing the pentafluoroethane can be used as an etching gas. The etching using pentafluoroethane can be performed under various dry etching conditions such as plasma etching and microwave etching.

The present invention is described in greater detail below, however, the present invention is not limited to these Examples.

RAW MATERIAL EXAMPLE OF PENTAFLUOROETHANE (RAW MATERIAL EXAMPLE 1)

Tetrachloroethylene and hydrogen fluoride were introduced into a first reactor filled with a catalyst to produce a gas mainly comprising 1,1,1-trifluoro-2,2-dichloroethane and 1,1,1,2-tetrafluoro-2-chloroethane which are intermediates. This gas was introduced together with HF into a second reactor to produce pentafluoroethane. The produced pentafluoroethane was distilled to obtain pentafluoroethane containing 0.5% of chloropentafluoroethane as an impurity.

This pentafluoroethane was reacted with hydrogen in the presence of a commercially available hydrogenation catalyst (reaction pressure: 0.35 MPa, reactor temperature: 280° C., $H_2$/chloropentafluoroethane molar ratio=5). The acid content was removed from the resulting mixed gas by a known method and the residue was purified by distillation, as a result, a distillate mainly comprising pentafluoroethane was obtained. This distillate was analyzed by gas chromatography and found to be a mixed gas having the composition shown in Table 1.

TABLE 1

| Components | Concentration (vol %) |
|---|---|
| $CF_3CHF_2$ | 99.7171 |
| $CF_3CF_2Cl$ | 0.0005 |
| $CF_3CH_2F$ | 0.0201 |
| $CF_3CH_3$ | 0.2621 |
| $CHF_3$ | 0.0002 |

PRODUCTION EXAMPLE OF CATALYST (CATALYST 1)

Chromium nitrate nonahydrate was dissolved in water and mixed with 28 wt % of aqueous ammonia while stirring to obtain a chromium hydroxide slurry. This was separated by filtration, thoroughly washed with water and then dried at 120° C. The obtained lump was pulverized, mixed with graphite and pelletized by a tablet molding machine. The obtained pellet was baked at 400° C. for 4 hours in a $N_2$ stream to obtain Catalyst 1 mainly comprising trivalent chromium oxide.

PRODUCTION EXAMPLE OF CATALYST (CATALYST 2)

Chloroplatinic acid was dissolved in water and a 3 mmϕ spherical alumina support was dipped in the resulting solution and adsorbed the platinum salt. Thereafter, the solvent was distilled off at a temperature of 100° C. and the residue was baked in an air at 300° C. and then hydrogen-reduced at 350° C. The percentage of platinum supported in the obtained Platinum Catalyst 2 was 0.25%.

EXAMPLE 1

A catalyst (Catalyst 1) (100 ml) was filled in an Inconel 600-made reactor having an inner diameter of 1 inch and a length of 1 m and kept at a temperature of 300° C. while passing a nitrogen gas. Subsequently, oxygen was supplied at a flow rate of 2.0 NL/hr, a gas having the composition shown in Table 1 was supplied at a flow rate of 38.0 NL/hr, the supply of nitrogen gas was then stopped and the reaction was started. After 2 hours, the outlet gas from the reactor was washed with an aqueous potassium hydroxide solution to remove the acid content, then contacted with Molecular Sieves 3A (produced by Union Showa K.K.) and dried. The resulting dried gas mainly comprising pentafluoroethane was collected under cooling and purified by distillation. The gas after the purification was analyzed by gas chromatography and found to be a gas having the composition shown in Table 2.

TABLE 2

| Components | Concentration [vol %] |
|---|---|
| $CF_3CHF_2$ | 99.9665 |
| $CF_3CF_2Cl$ | 0.0004 |
| $CF_3CH_2F$ | 0.0126 |
| $CF_3CH_3$ | 0.0204 |
| $CHF_3$ | 0.0001 |

EXAMPLE 2

Pentafluoroethane was obtained by the same operation as in Example 1 except for using Catalyst 2. The gas after the purification was analyzed and found to have the composition shown in Table 3.

TABLE 3

| Components | Concentration [vol %] |
|---|---|
| $CF_3CHF_2$ | 99.9840 |
| $CF_3CF_2Cl$ | 0.0004 |
| $CF_3CH_2F$ | 0.0101 |
| $CF_3CH_3$ | 0.0054 |
| $CHF_3$ | 0.0001 |

EXAMPLE 3

A nitrogen gas was supplied to a nickel-made reactor having an inner diameter of 1 inch and a length of 50 cm (employing a heating system using an electric heater; the reactor had been subjected to a passivation treatment with a fluorine gas at a temperature of 500° C.) through two gas inlets at a total flow rate of 30 NL/hr and the reactor was kept at a temperature of 420° C. Subsequently, HF was passed through the above-described two gas inlets at a total flow rate of 50 NL/hr and the mixed gas mainly comprising pentafluoroethane obtained in Example 1 was introduced through one gas inlet at a flow rate of 3.5 NL/hr. Also, a fluorine gas was introduced through another gas inlet at a flow rate of 3.85 NL/hr, thereby performing a reaction. After 3 hours, the outlet gas from the reactor was contacted with an aqueous potassium hydroxide solution and an aqueous potassium iodide solution to remove HF and unreacted fluorine gas. Thereafter, the gas was contacted with a dehydrating agent and thereby dried and the dried gas was collected under cooling and then purified by distillation. The gas after the purification was analyzed by the TCD method, the FID method and the ECD method of gas chromatography and the GC-MS method. The results are shown in Table 4.

TABLE 4

| Components | Concentration [vol %] |
|---|---|
| $CF_3CF_3$ | >99.9998% |
| $CF_4$ | <0.4 vol ppm |
| $CF_3CF_2Cl$ | <0.1 vol ppm |
| $CF_3CHF_2$ | <0.5 vol ppm |
| $SF_6$ | <0.4 vol ppm |

As is apparent from the analysis results shown in Table 4, the hexafluoroethane contained almost no other impurities and a high-purity hexafluoroethane was obtained.

RAW MATERIAL EXAMPLE OF PENTAFLUOROETHANE (RAW MATERIAL EXAMPLE 2)

Commercially available pentafluoroethane (containing as impurities 0.5% of chloropentafluoroethane) was reacted with hydrogen in the presence of a commercially available hydrogenation catalyst (reaction pressure: 0.35 MPa, reactor temperature: 280° C., $H_2$/chloropentafluoroethane molar ratio=5). The excess hydrogen and by-product hydrogen chloride were removed from the obtained mixed gas by purification by distillation, then the fine amount of acid content remaining was removed by washing by an alkali scrubber controlled in circulating fluid temperature to 10° C. The gas flowing out of the alkali scrubber was sampled and analyzed by gas chromatography, whereupon it was found to be a mixed gas having the composition shown in Table 5. Further, the moisture of the outflow was analyzed by a dew point meter, whereupon it was found to be 1.2 vol %.

TABLE 5

| Components | Concentration (vol %) |
|---|---|
| $CF_3CHF_2$ | 99.7240 |
| $CF_3CClF_2$ | 0.0006 |
| $CF_3CH_2F$ | 0.0199 |
| $CF_3CH_3$ | 0.2553 |
| $CHF_3$ | 0.0002 |

RAW MATERIAL EXAMPLE OF PENTAFLUOROETHANE (RAW MATERIAL EXAMPLE 3)

The same reaction was performed as shown in Raw Material Example 2. The obtained mixed gas was passed through a tube filled with molecular sieve, then purified by distillation to obtain a distillate mainly comprised of pentafluoroethane. This distillate was analyzed by gas chromatography, whereupon it was found to be a mixed gas having the composition shown in Table 6. Further, the moisture of the distillate was analyzed by a Karl Fisher moisture meter, whereupon it was found to be 7 vol ppm.

TABLE 6

| Components | Concentration (vol %) |
|---|---|
| $CF_3CHF_2$ | 99.7232 |
| $CF_3CClF_2$ | 0.0005 |

TABLE 6-continued

| Components | Concentration (vol %) |
|---|---|
| $CF_3CH_2F$ | 0.0187 |
| $CF_3CH_3$ | 0.2574 |
| $CHF_3$ | 0.0002 |

RAW MATERIAL EXAMPLE OF PENTAFLUOROETHANE (COMPARATIVE RAW MATERIAL EXAMPLE 2)

The same procedure was followed as shown in Raw Material Example 2 except for controlling the circulating fluid temperature of the alkali scrubber to 25° C. The composition of the gas flowing out from the alkali scrubber was similar to that in Table 5, but the moisture in the outflow was 3.1 vol %.

EXAMPLE 4

A catalyst (Catalyst 2) (100 ml) was filled in an Inconel 600-made reactor having an inner diameter of 1 inch and a length of 1 m and kept at a temperature of 290° C. while passing a nitrogen gas. Subsequently, dried air was supplied at a flow rate of 3.7 NL/hr, a gas having the composition shown in Table 5 (Raw Material Example 2) was supplied at a flow rate of 37.3 NL/hr, the supply of nitrogen gas was then stopped and the reaction was started. After 2 hours, the outlet gas from the reactor was washed with an aqueous potassium hydroxide solution to remove the acid content, then contacted with Molecular Sieves 3A (produced by Union Showa K.K.) and dried. The resulting dried gas mainly comprising pentafluoroethane was collected under cooling and purified by distillation. The gas after the purification was analyzed by gas chromatography and found to be a gas having the composition shown in Table 7.

TABLE 7

| Components | Concentration [vol %] |
|---|---|
| $CF_3CHF_2$ | 99.9784 |
| $CF_3CClF_2$ | 0.0005 |
| $CF_3CH_2F$ | 0.0156 |
| $CF_3CH_3$ | 0.0054 |
| $CHF_3$ | 0.0001 |

EXAMPLE 5

The same procedure was followed as in Example 4 except for using the crude pentafluoroethane of Raw Material Example 3 as a raw material to obtain pentafluoroethane. The gas after the purification was analyzed and found to have the composition shown in Table 8.

TABLE 8

| Components | Concentration [vol %] |
|---|---|
| $CF_3CHF_2$ | 99.9881 |
| $CF_3CClF_2$ | 0.0004 |
| $CF_3CH_2F$ | 0.0101 |
| $CF_3CH_3$ | 0.0013 |
| $CHF_3$ | 0.0001 |

COMPARATIVE EXAMPLE 1

The same procedure was followed as in Example 4 except for using the crude pentafluoroethane of Comparative Raw Material Example 1 as a raw material to obtain pentafluoroethane. The gas after the purification was analyzed and found to have the composition shown in Table 9.

TABLE 9

| Components | Concentration [vol %] |
|---|---|
| $CF_3CHF_2$ | 99.9329 |
| $CF_3CClF_2$ | 0.0004 |
| $CF_3CH_2F$ | 0.0141 |
| $CF_3CH_3$ | 0.0525 |
| $CHF_3$ | 0.0001 |

EXAMPLE 6

A nitrogen gas was supplied to a nickel-made reactor having an inner diameter of 1 inch and a length of 50 cm (employing a heating system using an electric heater; the reactor had been subjected to a passivation treatment with a fluorine gas at a temperature of 500° C.) through two gas inlets at a total flow rate of 30 NL/hr and the reactor was kept at a temperature of 420° C. Subsequently, HF was passed through the above-described two gas inlets at a total flow rate of 50 NL/hr and the mixed gas mainly comprising pentafluoroethane obtained in Example 4 was introduced through one gas inlet at a flow rate of 3.5 NL/hr. Also, a fluorine gas was introduced through another gas inlet at a flow rate of 3.85 NL/hr, thereby performing a reaction. After 3 hours, the outlet gas from the reactor was contacted with an aqueous potassium hydroxide solution and an aqueous potassium iodide solution to remove HF and unreacted fluorine gas. Thereafter, the gas was contacted with a dehydrating agent and thereby dried and the dried gas was collected under cooling and then purified by distillation. The gas after the purification was analyzed by the TCD method, the FID method and the ECD method of gas chromatography and the GC-MS method. The results are shown in Table 10.

TABLE 10

| Components | Concentration [vol %] |
|---|---|
| $CF_3CF_3$ | >99.9998% |
| $CF_4$ | <0.4 vol ppm |
| $CF_3CClF_2$ | <0.1 vol ppm |
| $CF_3CHF_2$ | <0.5 vol ppm |
| $SF_6$ | <0.4 vol ppm |

As is apparent from the analysis results shown in Table 10, the hexafluoroethane contained almost no other impurities and a high-purity hexafluoroethane was obtained.

As described in the foregoing pages, in accordance with the present invention, high-purity pentafluoroethane can be obtained. The pentafluoroethane obtained by the present invention can be used as a low-temperature refrigerant, an etching gas or a starting material for the production of high-purity hexafluoroethane.

We claim:

1. A process for producing pentafluoroethane, comprising the following steps:
    (1) a step of fluorinating tetrachloroethylene to obtain a crude pentafluoroethane, and
    (2) a step of bringing said crude pentafluoroethane into contact with oxygen and/or an oxygen-containing compound in the presence of a catalyst.

2. The process as claimed in claim 1, wherein the crude pentafluoroethane used in the step (2) is obtained through a further step of being contacted with hydrogen.

3. The process as claimed in claim 1, wherein the temperature in the step (2) is from 150 to 400° C.

4. The process as claimed in claim 1, wherein the catalyst is a supported or bulk catalyst mainly comprising trivalent chromium oxide.

5. The process as claimed in claim 1, wherein the catalyst is a supported catalyst mainly comprising at least one metal selected from the group consisting of palladium, rhodium, ruthenium, rhenium, platinum and gold.

6. The process as claimed in claim 4 or 5, wherein the support for use in the supported catalyst is alumina, fluorinated alumina or zeolite.

7. The process as claimed in claim 1 or 2, wherein said crude pentafluoroethane comprises at least one compound selected from the group consisting of fluoromethane, difluoromethane, fluoroethane, 1,1-difluoroethane, 1,2-difluoroethane, 1,1,1-trifluoroethane and 1,1,2-trifluoroethane as impurities.

8. The process as claimed in claim 1, wherein the total amount of impurities contained in said crude pentafluoroethane is 2 vol % or less.

9. A process for producing pentafluoroethane, comprising bringing a crude pentafluoroethane into contact with oxygen and/or an oxygen-containing compound at 150 to 400° C. in the presence of a catalyst mainly contact with oxygen and/or an oxygen-containing compound at 150 to 400° C. in the presence of a catalyst mainly comprising trivalent chromium oxide, and then separating impurities by distillation.

10. A process for producing pentafluoroethane, comprising bringing a crude pentafluoroethane into contact with oxygen and/or an oxygen-containing compound at 150 to 400° C. in the presence of a supported catalyst mainly comprising at least one metal selected from the group consisting of palladium, rhodium, ruthenium, rhenium, platinum and gold, and then separating impurities by distillation.

11. The process as claimed in claim 9 or 10, wherein said crude pentafluoroethane comprises at least trifluoroethane as impurities.

12. The process as claimed in claim 9 or 10, wherein the concentration of oxygen and/or oxygen-containing compound is from 0.1 to 20 vol %.

13. A process for producing hexafluoroethane, comprising the following steps:
    (1) a step of fluorinating tetrachloroethylene to obtain a crude pentafluoroethane,
    (2) a step of bringing said crude pentafluoroethane into contact with oxygen and/or an oxygen-containing compound in the presence of a catalyst to obtain pentafluoroethane, and
    (3) a step of reacting the pentafluoroethane obtained through the step (2) with a fluorine gas to obtain hexafluoroethane.

14. The process as claimed in claim 13, wherein obtained through a further step of being contacted with hydrogen.

15. A process for producing pentafluoroethane including a step of bringing crude pentafluoroethane into contact with oxygen or an oxygen-containing compound in the presence of a catalyst and with a moisture content included in the reaction substrate gas in said step of not more than 2 vol %.

16. The process as claimed in claim 15, wherein said crude pentafluoroethane is one obtained by a fluorination reaction for fluorinating tetrachloroethylene or its fluorinated product in the presence of a fluorination catalyst using hydrogen fluoride.

17. The process as claimed in claim 16, wherein the crude pentafluoroethane is obtained through said fluorination reaction, then a reaction of contact with hydrogen.

18. The process as claimed in claim 17, wherein said crude pentafluoroethane comprises at least one compound selected from the group consisting of fluoromethane, difluoromethane, fluoroethane, 1,1-difluoroethane, 1,2-difluoroethane, 1,1,1-trifluoroethane and 1,1,2-trifluoroethane as impurities.

19. The process as claimed in claim 15, wherein the total amount of impurities contained in said crude pentafluoroethane is 2 vol % or less.

20. The process as claimed in claim 15, wherein the temperature in said step is from 150 to 400° C.

21. The process as claimed in claim 15, wherein the concentration of oxygen and/or oxygen-containing compound in the reaction substrate gas is from 0.1 to 20 vol %.

22. The process as claimed in claim 15, wherein the catalyst used in said step is a supported or bulk catalyst mainly comprising trivalent chromium oxide.

23. The process as claimed in claim 15, wherein the catalyst used in said step is a supported catalyst mainly comprising at least one metal selected from the group consisting of palladium, rhodium, ruthenium, rhenium, platinum and gold.

24. The process as claimed in claim 22 or 23, wherein the support for use in the supported catalyst is alumina, fluorinated alumina or zeolite.

25. The process as claimed in claim 15, wherein said step is performed, then purification is performed by distillation.

26. A process for producing hexafluoroethane, comprising the following steps:
  (1) a step of bringing crude pentafluoroethane obtained by a fluorination reaction of fluorinating tetrachloroethylene or its fluorinated product in the presence of a fluorination catalyst into contact with an oxygen and/or oxygen-containing compound in the presence of a catalyst in a system with moisture of not more than 2 vol % and
  (2) a step of reacting the pentafluoroethane obtained through the step (1) with a fluorine gas.

27. The process as claimed in claim 26, wherein said crude pentafluoroethane used in the step (1) is obtained through said fluorination reaction, then a reaction of contact with hydrogen.

* * * * *